United States Patent [19]
Amici et al.

[11] Patent Number: 6,127,344
[45] Date of Patent: Oct. 3, 2000

[54] POLYNUCLEOTIDE IMMUNOGENIC AGENTS

[75] Inventors: Augusto Amici; Antonio Concetti; Franco Venanzi, all of Camerino, Italy

[73] Assignee: Universita' Degli Studi di Camerino, Camerino, Italy

[21] Appl. No.: 08/930,457

[22] Filed: Nov. 25, 1997

[30] Foreign Application Priority Data

Apr. 4, 1995 [IT] Italy .................................. MI95A0676

[51] Int. Cl.⁷ ........................ C12N 15/63; C12N 15/12; A61K 48/00
[52] U.S. Cl. ........................ 514/44; 536/23.1; 536/23.5; 435/320.1
[58] Field of Search ................ 536/23.1, 23.4, 536/23.5; 514/44; 435/320.1

[56] References Cited

U.S. PATENT DOCUMENTS

| | | |
|---|---|---|
| 4,935,341 | 6/1990 | Bargmann . |
| 5,401,638 | 3/1995 | Carney . |
| 5,422,262 | 6/1995 | Andersson . |
| 5,527,703 | 6/1996 | Cully . |

FOREIGN PATENT DOCUMENTS

90/14357  11/1990  WIPO .

OTHER PUBLICATIONS

Plowman, PNAS 87: 4905, 1990.

9$^{th}$ International Congress of Immunology, San Francisco, Calif., Jul. 23–29, XP000578979, D. Hu et al, "ErbB–2–neu DNA vaccine based immunotherepy", see Abstract 5162, 1995.

Ann. N.Y. Acad. Sci., Nov. 27, 1995, 772 P274–7, U.S., XP000578698, F.M. Venanzi et al, "neu/HER–2 cDNA vaccination and pregnacy loss".

Proc. Natl. Acad. Sci. USA, Oct. 1987, 84 (19) P6854–8, XP002011369, R. Bernards et al., "Effective tumor immunotherapy directed against an oncogene–encoded product using a vaccinia virus vector".

Science, vol. 247, Mar. 1990, DC, pp. 1465–1468, XP000293057, J.A. Wolff et al, "Direct gene transfer into mouse muscle in vivo".

Science, vol. 259, Mar. 1993, DC, pp. 1745–1749, XP002009751, J.B. Ulmer et al, "Heterologous protection against influenza by injection of DNA encoding a viral protein".

*Primary Examiner*—Nancy A. Johnson
*Attorney, Agent, or Firm*—Pennie & Edmonds LLP

[57] ABSTRACT

Polynucleotide immunogenic agents capable of inducing an immune response towards the members of the Epidermal Growth Factor Receptors (EGFR) family are disclosed.

6 Claims, 2 Drawing Sheets

POLYNUCLEOTIDE IMMUNOGENIC AGENTS

FIELD OF THE INVENTION

The present invention refers to expression vectors coding for fragments or full length erbB proteins (EGF receptors) as immunogenic agents, particularly her-2/erbB-2/neu receptor.

More particularly, the invention refers to the use of said expression vectors for the preparation of medicaments inducing a specific immune response in the host's cells.

BACKGROUND OF THE INVENTION

Different EGF receptors are known, such as EGFR1, HER-2/neu, HER-3, HER-4.

Particularly HER-2/neu has been proposed as target for antitumor strategies (WO 90/14357).

The proto-oncogene HER-2/neu codes for a 185 KDa membrane receptor protein (p185) (Schechter, A. et al. 1984, Nature 312/513).

The functions of HER-2/neu are presently not well known but they seem to be associated to the increase of tyrosine kinase activity (Di Fiore, P. et al. 1990 Mol. Cell. Biol. 10:2749).

Different ligands, which can induce both stimulatory and inhibitory signals depending on the ligand and/or the experimental conditions, were proposed for the receptor (Peles, E. et al. 1992 Cell. 69:205).

HER-2/neu is expressed during placentation and organogenesis (Kokay. Y et al. 1987 Proc. Natl. Acad. Sci. U.S.A. 84:8498; Knezevic V. et al. 1994 J. Anat. 1985:181) and it is detectable in small amounts in a number of epithelial/glandular adult tissues (Press. M. et al. 1990 Oncogenes. 5:953).

Mutations and/or overexpression of p185 are associated to tumor pathogenesis. The proto-oncogene is activated by punctiform mutations (Bargmann, C. & Weimberg R. A. 1988 EMBO J. 7:2043). In man mutations were not found and it was found that in the carcinomas of glandular origin (e.g. breast, ovary, lung and kidney adenocarcinomas), the transforming activity is related to an amplification/overexpression of p185 with normal structure.

The amplification of p185 has been associated with an unfavourable prognosis in patients with breast carcinoma (Yokota, J. et al. 1986 Lancet. i. 765; Slamon. D. J. et al. 1987 Science. 235:1772; Yonemura. Y. et al. 1991. Cancer Research. 51:1034, Gustarson. B. A. et al. 1992. Europ. J. Cancer. 28:263).

Recent studies also suggest a connection between the receptor overexpression and the phenomenon of drug resistance.

In fact, carcinomas overexpressing HER-2/neu are insensitive to 5-fluoruracyl treatment (Paikj S. M. et al. 1991 Proc. Am. Assoc. Cancer Resear. 32, 291). This was confirmed by transfection studies of HER-2/neu in breast carcinoma cell lines becoming resistant to Tamoxifen and cisplatin (Benz C. C. et al. 1992 Breast Cancer Research Treat. 24, 84).

The patients at stage I of breast carcinoma, with good prognosis but with immunochemically detectable HER-2/neu, relapse after chemiotherapeutic treatment (Alfred D. C. et al. 1992 J. Clin. Onc. 10, 599 and Gusterson B. A. et al. 1992 J. Clin. Onc. 10, 1049). Moreover, anti-HER-2/neu antibodies increase the cisplatin and tumor necrosis factor (TNF) cytotoxicity against the breast and ovary carcinoma (Hancock M. C. et al. 1991 Canc. Res. 51, 4575 and Hudziac R. M. 1989 Mol. Cell. Biol. 9, 1165). On the other hand, in the drug resistant cell lines, the amount of epidermal growth factor (EGF) receptor is increased (Meyers M. B. et al. 1986 Proc. Natl. Acad. Sci. U.S.A. 83, 5521), and the antibodies against said receptors increase the cytotoxic effects of drugs (Aboud-Pirak E. et al. 1988 J. Natl. Canc. Inst. 80, 1605; Baselga J. et al. 1993 J. Natl. Canc. Inst. 85, 1327).

Similarly to antibodies also EGF increases the cytotoxic effect of alkylating agents such as cisplatin, of ionizing rays, of mytomicin, of 5-fluoruracyl and of adriamycin (Christen R. D. 1990 J. Clin. Inv. 86, 1632; Kowk T. T. et al. 1989 J. Natl. Canc. Inst. 81, 1020; Amagase H. et al. 1990 J. Pharm. Dyn. 13, 263; Amagase H. et al. XXX Jpn. J. Canc. Res. 80, 670; Kowk T. T. et al. 1991 Int. J. Cancer 49, 73).

The small amounts of p185 expressed in normal epithelia in comparison to the larger amounts in cancer tissues induced to believe that the receptor may act as target antigen for passive immunotherapeutic strategies, (e.g. by administering monoclonal antibodies). It is known, for instance, that some anti-p185 monoclonal antibodies can inhibit the growth of breast carcinoma cells both in vitro and in nude mice (Marx. J. 1993 Science 259:226).

Recently it has been demonstrated that anti-erbB-2 monoclonal antibodies can exert a cytostatic effect on tumor by down-regulation of the receptor itself (Katsumatu M. et al., 1985, Nature Medicine 1:644–648).

Although active immunization strategies (vaccination) were proposed for this antigen, this hypothesis was prejudiced by the possibility that the induced immunity could be toxic for the epithelia physiologically expressing this antigen.

On the other hand, the inoculation of recombinant vaccinia viruses expressing the extracellular domain of neu oncogene completely and specifically protected mice against tumor cells expressing this antigen (Bernards. R. et al. 1987 Proc. Natl. Acad. Sci. U.S.A. 84:6854).

Since the growth factors and their receptors play a central role as autocrine and paracrine regulatory circuits not only during tumorigenesis but also during embryonic development, experimental models based on both these developmental processes are particularly significant for the purposes of this invention.

SUMMARY OF THE INVENTION

The present invention refers to the use of substantially pure cDNA coding for homologous foreign HER-2/neu or for another EGF receptor or for partial sequences of the said receptors, for the preparation of immunogenic medicaments for use in oncological immunotherapy.

The invention refers also to expression vectors, such plasmids, containing one of the above mentioned cDNA.

The invention refers also to the use of said cDNA for the isolation and selection of B-lymphocytes to be used in the production of specific monoclonal antibodies.

DETAILED DESCRIPTION OF THE INVENTION

Figure 1:
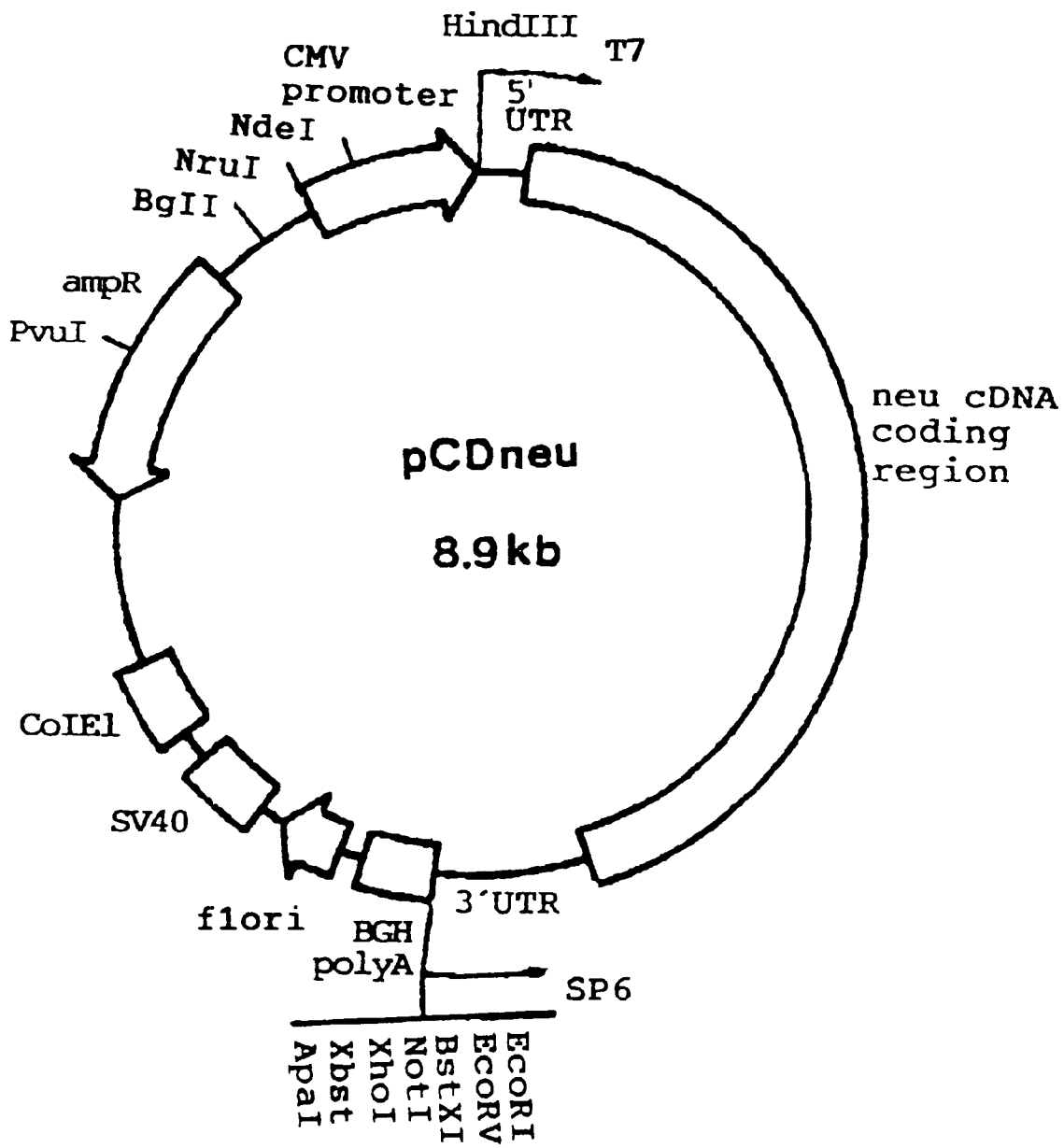
FIG. 1 pCDneuNT construct.
Figure 2:
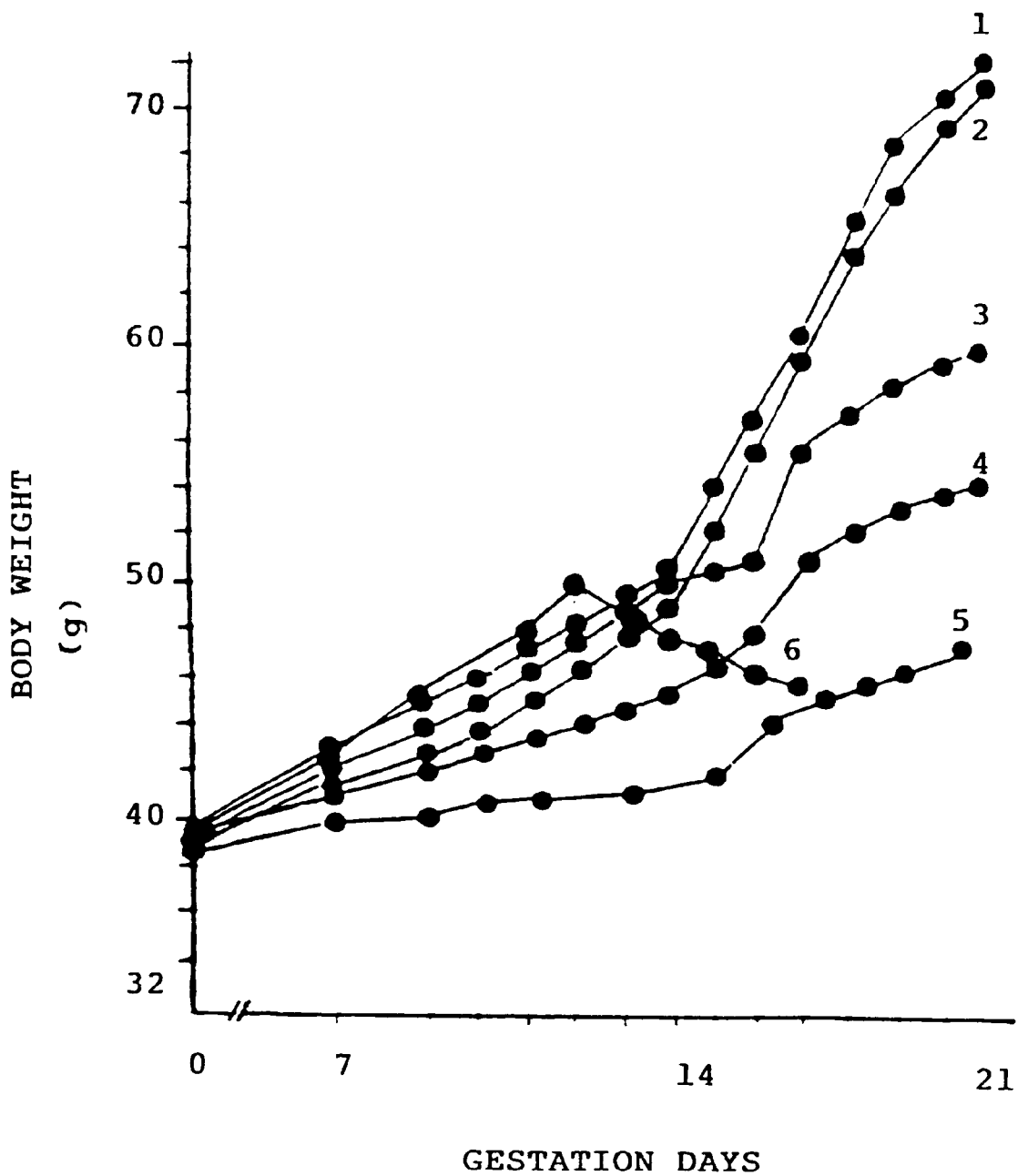
FIG. 2 Effect of pCDneuNT vaccination on Pregnancy. Swiss (outbred) female mice (3 to 6) were immunized con pCDneuNT and after two weeks from last boost, mated for one day with males. The mating was assessed by the presence of spermatic cells in vaginal smear (first day of pregnancy). The data reported refer to body growth rates during pregnancy. Mice 1–2 are non immunized animals (control).

According to the invention, the in vivo administration of non infectious cDNA sequences coding for receptor of EGF, particularly of HER-2/neu, induces an immune response useful in antitumoral therapy.

In fact, such therapy significantly reduces the tumoral masses and inhibits the growth of experimentally induced syngenic tumors.

The effectiveness of the in vivo immunization was also shown using the pregnancy model. The embryonic and tumoral development share in fact, at least in their initial step, some relevant biological features e.g. the increased expression of erbB-2/neu gene.

In fact, the immune response in pregnant mice turned out to be selective against the antigen so as to damage the embryonic development, with negligible or no cytotoxic effects on differentiated adult epithelia. Said selectivity, according to the observed specific cytotoxic effects, is associated with the production of anti p185 antibodies recognizing epitopes of the receptor extracellular domain, showing an unusual resistance to the formaldheyde treatment. Said selectivity is further confirmed by the ability of the antibodies to interact with NHI-3T3 fibroblasts transformed by the pCDneuNT plasmid, and with the breast tumor cell line SK-BR3 overexpressing c-erbB-2, and by staining histological samples both from human breast infiltrating ductal carcinomas and from nodular mammary adenocarcinoma in neu transgenic mouse.

Since the inhibition of two processes, tumorigenesis and pregnancy, following immunization is surprisingly limited to the structures overexpressing erbB-2/neu in developing tissues and not in differentiated tissues, it follows that the DNA vaccination with sequences coding for EGF receptors may be used as a specific and effective antitumor therapy.

The invention has several advantages in comparison with the known immunotherapies. In comparison with the passive transfer of monoclonal antibodies, the polynucleotide vaccination has the advantage of inducing not only the production of antibodies but also the production and expansion of cytotoxic CD8+MHC class 1 T lymphocytes.

Even in comparison with the use of peptides with selected sequences representing epitopes of the protein against which the immune response has to be raised, the advantages of the present invention are remarkable: in fact the latter is not limited to selected aplotypes, since potentially T cell repertoire for cryptic and subdominant epitopes can be activated by homologous foreing antigen in order to obtain Th responses spontaneously selected in each subject on the basis of his own aplotype.

Moreover, as high affinity antibodies are produced by the conventional immunization when the antigen concentration becomes limitant, the expression of low concentration antigens, as observed with the polynucleotide immunization, may induce the development of high affinity antibodies already in the first immunization steps.

In comparison to the immunotherapies with viral vectors, the administration of naked DNA is remarkably safer since: 1) DNA is not infective; 2) there is no integration of the antigenic DNA in the host chromosome (the expression vector remains in episomal form for about one week).

The cytotoxic effects induced by the viral immunization may decrease the number of host cell expressing viral antigens.

Moreover, many viruses negatively regulate the host's transcriptional factors, which may on one side decrease the expression of MHC I class molecules on the cell surface and on the other side impair the normal processing of the intracellular proteins also in this way decreasing the presence of epitopes on MHC molecules. Further advantages of the invention are provided by the easy availability and control of the antigens DNA sequences.

According to the invention, the immunogenic agent may be prepared by known methods. The DNA sequences of EGFR or HER-2/neu are known and can be prepared by conventional methods such as PCR, recombinant DNA etc. It is optionally possible to use also partial sequences of genes or chimeric structures, providing that the resulting expression product has suitable immunogenic properties. For instance, the agent can be prepared by linking the EGFR DNA to one or more sequences (promoter and replication origin) allowing the expression of said DNA in tissues and in microorganisms for the preparation process. The control sequences may be obtained from plasmids or viruses such as SV40 or cytomegalovirus (CMV) or Rous sarcoma virus (WO 94/21707 of 29.09.94).

The agent may be administered according to known methods (Donnelly J. J. et al. 1994. The immunologist 2:1).

The effects of intramuscular injections of DNA were considered as a new vaccination tool for the treatment of infectious diseases. In addition to the intramuscular route, other administration routes of DNA are possible, e.g. the parenteral and mucosal route (Proc. Natl. Acad. Sci. U.S.A. 1986 83, 9551; WO 90/11092 of 4.10.90). DNA may also be adsorbed on gold microparticles for the transcutaneous administration by means of balistic apparatuses (Johnston, 1992 Nature. 356, 152).

Moreover, in view of the previous arguments, the immunization has remarkable advantages in the preparation of the monoclonal antibodies having in vivo biological activity. In fact, the DNA vaccination with said oncogene or related proto-oncogene (neuNT, neu) allows the selection, directly from the animal which responded to the treatment, the lymphocyte lines isolated from the spleen to be used for the preparation of said monoclonal antibodies. Similarly said vaccine may be used for the selection of human lymphocyte lines from peripheral blood for the production of monoclonal-antibodies for use as adjuvants, optionally conjugated with cytotoxic molecules to be used in passive immunotherapy.

EXAMPLE 1.1 Cloning of pCDneuNT expression vector.

All the enzymatic manipulations of the DNA, cloning and characterisation of the recombinant constructs have been carried out with strict adherence to the methods described by Maniatis ("Gene Cloning"). The plasmid pSV2 neuNT which contains the cDNA encoding the entire neuNT oncoprotein (ref. Weinberg) was digested with the enzymes HindIII, Sal I and EcoRI. Digestion with EcoRI generates two fragments of the original plasmid (PSV2neo). The combined digestion with HindIII/SalI generates the full-length cDNA (about 4600 bp). The HindIII/SalI gene segment has then been cloned into the intermediate vector pSP64, previously digested with the enzymes HindIII/SalI. The recombinant construct pSP64 neuNT (Amersham) has been cloned and characterised as described previously. pSP64 neuNT was digested with HindIII/EcoRI generating two fragments: 1) 3000 bp (pSP64); 2) about 4600 bp (neuNT). Fragment 2 was cloned in pCDNA3 neo ( ), previously prepared and digested with the enzymes HindIII/EcoRI. The final recombinant vector was utilised for the immunization procedures.

1.2 Immunization of mice and rats.

Female outbred Swiss, CD1 and Balb-c and inbred FVBN and Balb-c $H_2^D$ mice were anaesthetised with a nembutal-Equithesinain solution at a dose of 0.3 ml/100 g body weight. The injections with an insulin syringe (1 ml) delivered 100 μl of a DNA solution in saline (1 mg/ml). The animals were immunised with three inoculations carried out at biweekly intervals. The same immunization schedule was used on Wistar rats.

1.3 In vivo expression of the antigen.

To verify the capability of the pCDneuNT plasmid of expressing the neuNT antigen in vivo, the animals were sacrificed 48 hours from the injections and the quadriceps femoral muscles were removed in one piece. The muscular tissue was homogenised in the presence of protease inhibitors and of non-ionic detergent. The total extracted proteins were then assayed in dot blots for the presence of the p185 antigen using monospecific rabbit polyclonal anti-neu IgG antibodies (K15) SC-07 (Santa Cruz Biotechnology, USA), following a standard procedure (both the dot-blotting and every other immunochemical technique reported from here onwards have been carried out according to the procedures indicated in: "Antibodies: a laboratory manual" 1988 Cold Spring Harbor Laboratory Ed. Harlow/David Lane).

The results have evidenced that only the proteins derived from the muscles in which pCDneuNT had been injected, and not those treated with the control plasmid, were able to bind to anti-p185 antibodies, from which one can conclude that the pCDneuNT plasmid is able to direct the synthesis of the p185 molecule inside the muscular fibres.

1.4 Immunoreactivity in the host.

i) mouse.

It is known that the capability of responding to exogenous antigens varies greatly according to the animal strain used. Also with respect to the immunogenicity of neu rat in the mouse, it is known from the literature (Bernards R. et al. 1987 Proc. Natl. Acad. Sci. USA 89: 6854–6858) that antibody production against the extracellular domain (ECD) of the oncogene by immunization with a vaccine virus is restricted to hosts that belong to heterozygous populations. It was therefore necessary to assay the anti-p185 immunoreactivity of different strains following the immunization with the gene.

Outbred Balb-c, CD1 or Swiss or inbred Balb-c $H_2D$ or FVBN mice of eight weeks were inoculated either with 100 μg control plasmid or with an equal dose of pCDneuNT according to the previously described schedule. As controls, the preimmune sera from the same animals were used.

The production and specificity of the anti-p185 antibodies was evaluated through the Western blotting technique, using as antigen source cellular lysates from 3T3 cells transformed with pSVneuNT (Bernards, R. et al., 1987, Proc. Natl. Acad. Sci. USA 84: 6854–6858). The results demonstrate that both the homo- and heterozygotic mice were able to recognise the rat protein, following the immunization with pCDneuNT.

The formation of antigen antibody complexes was further evidenced through the immunochemical analysis of murine mammary tumors in transgenic MMTV, neuN mice characterised by the overproduction of the receptor (C. T. Guy et al. 1992 PNAS 89: 10578–582).

Sections of mammary carcinomas of MMTV, neuN transgenic mice (3–5 u) were prepared following the same procedures reported above and incubated with antisera derived from mice immunised either with pCDneuNT or with control plasmids (dilution of the antiserum 1/30) followed by the addition of goat anti-mouse antibodies conjugated with peroxidase (1/100 dilution). It has been found that only the pCDneuNT antisera were able to develop a clear staining on the membrane of the tumor cells.

ii) rat:

The immunization with pCDneuNT in mice represents a classical xenogenic immunization given that the procedure presents an immunogenic protein of a species (rat) in a host of a different species (mouse). To verify if the anti-p185 immunity could be generated through immunization of the gene in an entirely syngeneic system, Wistar rats (outbred) have been inoculated with the pCDneuNT plasmid using the same immunization scheme as employed in the mouse. No anti-p185 seropositivity was evidenced in the treated animals even increasing the quantity inoculated in the muscle up to 0.8 mg. This result is in accordance with that reported by Bernards R. et al. Proc. Natl. Acad. Sci. USA 84: 6854–6858 (1987) and reinforces the concept that the murine model presents an elevated tolerance (with respect for example to the human) towards the self antigen (Houghton A. N. J. Exp. Med. 180:1–4 (1994)). It is still possible in any case that the simultaneous inoculation of the vector and of drugs through the same or other routes could reduce or even avoid the phenomenon of tolerance towards self p185.

1.5 Antibodies specificity i) Anti-rat P185 IgGs as autoantibodies.

Given that the injection of rat pCDneuNT is able to induce the production of antibodies reactive against the rat receptor (reactivity against neuNT), it was reasonable to expect, for simple philogenetic reasons, that the same mouse antibodies should be able to recognise both the mouse receptor itself (self antigen) and the homologous human variant erbB-2. The immunoreactivity of the circulating anti-p85 antibodies in the mouse towards the self antigen was evidenced by histochemical means.

In the mouse as in the adult rat, the neu proto-oncogene is physiologically expressed in epithelial/endocrine tissues such as the lung, liver, kidney, gut and in the basal layer of the epidermis cells (Knerewik V. et al. 1994 J. Anat. 181:1985). In the experiments, the animals were sacrificed with an overdose of ether vapours and sections (3–5 u) were prepared from tissues that constitutively express erbB-2/neu, such as the kidney, from material prepared with the method by Carnoix, and prepared for the histological analysis according to a standard procedure. The samples were then incubated with the anti-p185 antisera or with control sera at a 1:60 dilution and successively with goat anti-mouse antibodies conjugated with alkaline phosphatase (dilution 1/100). The results clearly prove: a) the reactivity of the circulating p185 antibodies towards the kidney cells of the same animal and b) the absence of recognition of the same cells by antibodies induced following immunization with the control pCDNA-3. The identity of murine p185 as the target antigen was then verified by Western blotting using mouse kidney homogenate extracts incubated with immune mouse serum or with the rabbit anti neu K15 SC-07 antibodies previously described.

ii) Anti-rat p185 IgGs cross-react with human receptor.

The possibility that the anti-p185 antibodies produced by the mice immunised with pCDneuNT could also be able to recognise the human p185 homologous variant erbB-2, has resulted from studies of immunofluorescence in confocal microscopy using SKBR3 cells derived from a human mammary carcinoma cell line, that overexpress p185$^{erbB-2}$ ($10^6$ receptor molecules/cell; Kraus M. H. et al. 1987 EMBO J. 6: 605–610.

After the preparation of slides of SKBR3 cells, grown on cover-slip slides, fixed, either with a mixture of cold methanol-acetone (1:1 V/V) (permeabilised cells) or with 2% paraformaldehyde (non permeabilised cells), the cellular samples were incubated with anti-p185 antisera at a 1/30 final dilution, and the antigen-antibody reaction was evidenced using sheep anti-mouse IgG antibodies conjugated with fluorescein (FITC) (Boehringer) (dilution 1:60). The mounted slides were examined under a laser confocal microscope (BioRad MRC800K) with a triple Argon laser and a 60× oil immersion objective.

The reactivity of both the non permeabilised cells that showed a strong fluorescence distributed in a diffuse way on the extracellular side of the plasma membrane, and of the permeabilised ones, that presented a well defined fluorescence in the perinuclear region, indicated that the anti-p185 antibodies were composed of a mixed population of immunoglobulins capable of recognising both the extracellular and intracellular domain of the antigen.

The confirmation that the murine anti-p185 antibodies were able to recognise the human variant of the antigen was obtained by western blotting using cell lysates of SKBR3, T23.1 (3T3 NIH fibroblasts transfected with retroviral erbB-2 DNA), and control 3T3 cells. The results indicated clearly the presence, in the sera of mice immunised with pCDneuNT, of anti-p185 antibodies, detected with biotinylated goat anti-mouse IgG antibodies (Santa Cruz Biotechnology Inc) reacted with peroxidase (horseradish) conjugated with streptavidin (1:200).

The fact that the anti-p185 antibodies could interact with human erbB-2, and recognise the extracellular domain of the protein even after strong fixation procedures, suggested the possibility of analysing, with these antibodies, the overexpression of erbB-2/neu that can be observed in some human mammary adenocarcinomas.

Thus, 21 samples corresponding to the ductal infiltrating carcinoma histotype obtained from surgical resection and taken from the Pathological Anatomy Service of the "Ospedale Civile" of Macerata, were examined by histochemistry using the same procedures of fixation, inclusion into paraffin blocks, staining of the tissue sections followed for the murine tissues.

The anti-p185 positivity of the sera from female mice immunised with pCDneuNT was observed only in the 8 out of 21 cases that had resulted positive for erbB-2 when stained with commercially available antibodies in an absolutely superimposable manner.

In order to verify if the murine anti-erbB-2/neu antibodies could react with other members of the EGFR family members, such as for example EGFR-1, the murine antibodies were incubated with cells of the human A431 epidermoid carcinoma line known to express a very high number of EGFR-1 receptor molecules (2–3×10$^6$/cell) on their surface. The immunoreactivity of the anti-p185neu antibodies with respect to the p170$^{EGFR-1}$ was analysed by immunofluorescence with the FACS scann. Controls for both the antigen and the antibodies were prepared using respectively the lymphoid cells CEM (human cells derived from a patient with acute lymphoblastic leukaemia, that do not express EGFR-1) as negative control, and monoclonal antibodies W600 (Dr. P. G. Natali, Istituto di ricerca sperimentale Regina Elena, Roma) specific for the ECD of erbB-2/neu and that do not cross react with the EGFR-1 antigen, as a positive control. The cells, after incubation with the second anti-mouse FIT conjugated antibody, were analysed using a Bekton Dickinson FACS (argon laser light of excitation, 488 nm. Measure of the emitted light at 525 nm). The results obtained indicate clearly that the anti-p185 immunoglobulins present in the antisera of the immunised mice behave exactly like the W600 MAb, that is they do not express reactivity towards p170$^{EGFR-1}$.

1.6 In vitro activity of the p185 antisera.

Inhibition of the growth of SKBR3 cells by the anti p185 antisera.

SKBR3 cells were plated in 35 mm culture plates at the concentration of 10$^3$ cells/plate. 30 μl (about 300 μg of total IgG) of anti-p185 antisera and control antisera were added, in duplicate, at day 0. After one week, the cells were removed from the plate and their number was determined with a haemocytometer. The immunoglobulins from pCDneuNT immunised mice, of the IgG isotype, were able to inhibit the growth of SKBR3 cells.

1.7 Biological effects of the immunization.

i) Toxicity of the treatment.

The non production of circulating anti-DNA antibodies following the administration of the DNA vaccine was demonstrated using a commercially available ELISA kit (INOV Diagnostics Inc; San Diego, Calif.) that uses highly purified calf thymus double helix DNA as antigen. Variations in the IgM and IgG content were not specifically noted.

Several assays of haematologic and serum parameters, such as haemochrome, VES leukocyte formula, proteinaemia etc, have been carried out, all resulting within the normal range.

ii) Histopathological examination of tissues.

The fact that the immunised animals possess circulating antibodies that can interact with the neu receptor of their own tissues, leads to the possibility that pathological phenomena of an autoimmune type could arise through mechanisms mediated by for example the complement system (Complement Dependent Cytotoxicity, CDC) and/or natural killer cells (Antibody Dependent Cellular Cytotoxicity, ADCC) (Stribling et al. Proc. Natl. Acad. Sci. USA 89: 11277–11281 (1992)).

In order to verify such a hypothesis, the animals have been sacrificed with an overdose of ether vapours and the tissues that constitutively express erbB-2/neu, the kidney, gut, ovary, placenta and the mammary gland were fixed using conventional methods, the inclusion in paraffin blocks, cutting of the sections (3–5 μ) and deparaffination of the same have been carried out using standard procedures described previously. The samples treated in such a way were stained with haematoxilin and eosin.

Repeated histological examinations have constantly excluded the presence, in the immune mouse, of even minimal traces of lesions (evidenced for example by necrotic areas, lymphocyte infiltrations or other) in the pcDNAneuNT immunised animals. One can therefore state that the DNA vaccination is deprived of apparent toxicity both at the general and tissue level, indeed, despite the fact that the animal possesses antibodies against its own receptor, no sign of systemic or organ specific autoimmune pathology was observed.

To summarise: i) the animals feed and drink normally even one year after the vaccination; ii) they show an excellent fur quality; no alteration in their individual or social behaviour is noted; iii) several haematological parameters remain within the normal range; iv) the tissues in which neu is expressed do not present any lesion upon histological examination; v) the vaccination does not produce a detectable increase in circulating anti-DNA IgM and/or IgG antibodies.

iii) Effect of the vaccination with pCDneuNT on pregnancy in mice.

83% of female Swiss mice immunised (n=16) developed circulating anti-p185 antibodies. 10 seropositive animals were caged with males and mating was confirmed the day after (day 1 of gestation) by the presence of sperm cells in the vaginal smears. The body weights of the pregnants were recorded every two days. Seven out of ten female mice showed a reduced number of offspring per litter (5±2 compared to 13±3 in the controls) while the hysterectomy of the remaining three demonstrated full fetus reabsorption.

More marked was the effect of said vaccination on the inbred strains such as Balb/c $H_2^D$ that all showed a marked development of anti-p185 antibodies. 14 out of 19 vaccinated female mice, did not give birth at all, the others gave birth with a limited number of offsprings (1–2) compared with the control ones (15 animals: 8±3 offsprings).

On the contrary, no significant difference in the fecundation capacity was observed between the groups of non-treated mice and of mice immunised with the control plasmid or of rats immunised with pCDneuNT (syngeneic immunization).

iv) Histopathological examination of the Placenta and of the mammary tissue.

Seven p185 serum positive pregnant mice were sacrificed at day 18 of gestation for the hystological examination of placenta and mammary glands.

Sections (3–5 μ) of formalin fixed tissues were stained as previously described. All specimens were found to be devoid of hystopathological elements.

v) Effect on mouse tumors.

In order to verify the immunotherapeutic effect of the vaccination against erbB-2/neu with respect to tumors which overexpress this proto-oncogene, tumors were induced in outbred mice according to the following procedure: clones of NIH3T3 fibroblasts transfected with CMVneuNT and which express substantial levels of the receptor on the cell surface, were inoculated in Swiss CD1 mice two weeks after the end of the immunization cycle. The growth of the neoplastic masses at the site of injection was measured with time through a calibration method. In the non immunised mice or in those immunised with the control plasmid, the cells grew progressively for about three weeks (See Table). A radically different result was obtained when the transformed fibroblasts were inoculated in mice immunised with pCDneuNT in which no development of neoplastic masses was observed at the site of injection.

These results demonstrate therefore that the immunization with the CMVneuNT plasmid in the form of an injectable physiological solution of naked DNA is able to drastically and specifically inhibit the attachment and dissemination of the tumor cells that overexpress the neu oncogene.

TABLE

| | Tumor area (mm²) | | |
| --- | --- | --- | --- |
| | 1W | 2W | 3W |
| A | 150 ± 60 | 380 ± 50 | 580 ± 70 |
| B | 150 ± 60 | 410 ± 65 | 550 ± 40 |
| C | nd | nd | nd |

Inhibition of tumor growth. 10 weeks old Swiss CD1 (Charles River) female mice (12 per group) were immunized with plasmid DNA encoding both for neuNT (C) and for irrelevant gene (p24-FIV) (B) as described in the test. Mice in group A received saline injections. After two weeks the mice were inoculated with $10^7$ 3T3 NIH cells transfected with neuNT. W, week after challenge. The data refer to mean square of the tumor (±SD).

nd, tumor not detectable.

What is claimed is:

1. A method for inducing immunity against a proto-oncogene or oncogene of the epidermal growth factor (EGF) receptor family in an animal, which comprises administering to an animal in need of such induced immunity an expression vector comprising the full length cDNA encoding for the proto-oncogene or oncogene of the EGF receptor family functionally linked to the cytomegalovirus (CMV) promotor for directing the expression of said cDNA.

2. A method according to claim 1, wherein the oncogene is the HER-2/erb-2/neu oncogene.

3. A method according to claim 1, wherein the administering is by intramuscular injection, parenteral injection, by a mucosal route, or by transcutaneous administration.

4. A method according to claim 1, wherein the expression vector is a pCDneuNT plasmid.

5. A method according to claim 1, wherein the animal is a mouse.

6. A method according to claim 1, wherein the animal is a rat.

* * * * *